United States Patent
Lim et al.

(10) Patent No.: US 10,531,967 B2
(45) Date of Patent: Jan. 14, 2020

(54) WALKING ASSISTANCE APPARATUS AND OPERATION METHOD OF THE SAME

(71) Applicant: Samsung Electronics Co., Ltd., Suwon-si, Gyeonggi-do (KR)

(72) Inventors: Bokman Lim, Yongin-si (KR); Youngjin Park, Seoul (KR); Keehong Seo, Seoul (KR); Youngbo Shim, Seoul (KR); Seungyong Hyung, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 796 days.

(21) Appl. No.: 15/013,157

(22) Filed: Feb. 2, 2016

(65) Prior Publication Data
US 2017/0056211 A1    Mar. 2, 2017

(30) Foreign Application Priority Data
Sep. 2, 2015   (KR) ................. 10-2015-0124056

(51) Int. Cl.
| | | |
|---|---|---|
| *A61H 3/00* | (2006.01) | |
| *A61F 2/72* | (2006.01) | |
| *A61B 5/107* | (2006.01) | |
| *A61B 5/11* | (2006.01) | |

(52) U.S. Cl.
CPC .............. *A61F 2/72* (2013.01); *A61B 5/1071* (2013.01); *A61B 5/112* (2013.01); *A61H 3/00* (2013.01)

(58) Field of Classification Search
CPC .............. A61H 3/00; A61H 2201/5069; A61H 2201/5079; A61H 2201/5007; A61H 2201/165; A61F 2/72; A61F 2/68; B25J 9/00; B25J 11/00; B25J 9/0006; A61B 5/112; A61B 5/04888
See application file for complete search history.

(56) References Cited

U.S. PATENT DOCUMENTS

| | | | | |
|---|---|---|---|---|
| 7,942,833 | B2 * | 5/2011 | Yasuhara ............... | A61H 3/00 |
| | | | | 135/67 |
| 8,986,233 | B2 | 3/2015 | Aoki et al. | |
| 10,016,330 | B2 * | 7/2018 | Endo ..................... | A61H 3/00 |
| 2004/0246769 | A1 * | 12/2004 | Ido ........................ | A61B 5/1038 |
| | | | | 365/154 |

(Continued)

FOREIGN PATENT DOCUMENTS

| | | |
|---|---|---|
| JP | 2002301124 A | 10/2002 |
| JP | 4008465 B2 | 11/2007 |

(Continued)

*Primary Examiner* — Michael J Tsai
*Assistant Examiner* — Christopher E Miller
(74) *Attorney, Agent, or Firm* — Harness, Dickey and Pierce, P.L.C.

(57) ABSTRACT

A walking assistance apparatus may include a driver configured to assist movements of a first joint related to a right leg of a user and a second joint related to a left leg of the user, a sensor configured to measure a first joint angle corresponding to the first joint and a second joint angle corresponding to the second joint, and a controller configured to generate a walking assist profile based on a previous step of the user, modify the walking assist profile based on the first joint angle and the second joint angle, and control the driver based on the modified walking assist profile.

15 Claims, 14 Drawing Sheets

(56) References Cited

U.S. PATENT DOCUMENTS

| | | | |
|---|---|---|---|
| 2006/0211956 A1* | 9/2006 | Sankai | A61B 5/04888 601/5 |
| 2008/0161937 A1* | 7/2008 | Sankai | A61H 3/008 623/25 |
| 2008/0234608 A1* | 9/2008 | Sankai | A61B 5/04888 601/5 |
| 2009/0062884 A1* | 3/2009 | Endo | B25J 9/0006 607/49 |
| 2009/0131839 A1* | 5/2009 | Yasuhara | A61F 5/0102 601/5 |
| 2009/0192414 A1* | 7/2009 | Yasuhara | A61H 3/00 600/587 |
| 2009/0227424 A1* | 9/2009 | Hirata | A61B 5/1038 482/7 |
| 2009/0270766 A1* | 10/2009 | Yasuhara | A61H 3/00 600/595 |
| 2010/0076360 A1* | 3/2010 | Shimada | A61B 5/1038 602/23 |
| 2010/0132464 A1* | 6/2010 | Yasuhara | A61B 5/1038 73/504.12 |
| 2012/0016278 A1* | 1/2012 | Nakashima | A61H 1/024 601/34 |
| 2012/0215140 A1* | 8/2012 | Hirata | A61H 1/0244 601/35 |
| 2013/0123669 A1* | 5/2013 | Kinoshita | A61B 5/112 600/595 |
| 2013/0138020 A1* | 5/2013 | Yasuhara | A61H 3/00 601/35 |
| 2014/0012164 A1 | 1/2014 | Tanaka | |
| 2014/0121575 A1 | 5/2014 | Yasuhara et al. | |
| 2014/0221894 A1* | 8/2014 | Nagasaka | A61H 3/00 602/23 |
| 2015/0094823 A1* | 4/2015 | Moon | A61H 3/00 623/27 |
| 2015/0119996 A1* | 4/2015 | Choi | A61F 2/68 623/24 |
| 2015/0134079 A1* | 5/2015 | Yoon | A61F 2/68 623/27 |
| 2015/0190923 A1* | 7/2015 | Seo | B25J 9/0006 602/16 |
| 2015/0196403 A1* | 7/2015 | Kim | A61F 2/70 623/24 |
| 2016/0101515 A1 | 4/2016 | Lim et al. | |
| 2017/0202724 A1* | 7/2017 | De Rossi | A61H 3/00 |

FOREIGN PATENT DOCUMENTS

| | | |
|---|---|---|
| JP | 2009095577 A | 5/2009 |
| JP | 2010148637 A | 7/2010 |
| JP | 2013111368 A | 6/2013 |
| JP | 2013111408 A | 6/2013 |
| JP | 2014-018536 A | 2/2014 |
| KR | 1020090104261 A | 10/2009 |
| KR | 20150053065 A | 5/2015 |

* cited by examiner

WALKING ASSISTANCE APPARATUS AND OPERATION METHOD OF THE SAME

CROSS-REFERENCE TO RELATED APPLICATION

This application claims under 35 U.S.C. § 119 to Korean Patent Application No. 10-2015-0124056, filed on Sep. 2, 2015, in the Korean Intellectual Property Office, the entire disclosure of which is incorporated herein by reference for all purposes.

BACKGROUND

1. Field

At least one example embodiment relates to a walking assistance apparatus and/or an operation method of the walking assistance apparatus. For example, at least some example embodiments relate to a method and/or apparatus for controlling a gait assistance based on information associated with a joint angle of a user.

2. Description of the Related Art

With the onset of rapidly aging societies, many people may experience inconvenience and pain from joint problems, and interest in walking assistance apparatuses enabling the elderly or patients with joint problems to walk with less effort, may increase.

A walking assistance apparatus may assist a user to move a joint and a muscle, thereby enabling the user to walk or improving a gait of the user. Also, the walking assistance apparatus may perform a feed forward control based on information associated with a previous step of the user, thereby enhancing gait safety.

When the user suddenly stops walking, or reduces or increases speed while walking, the user may experience inconvenience due to the feed forward control performed by the walking assistance apparatus. Also, it may be difficult to naturally apply a radical change in a gait style of the user to the walking assistance apparatus using a limited type of sensor.

SUMMARY

Some example embodiments relate to a walking assistance apparatus.

In some example embodiments, the walking assistance apparatus may include a driver configured to assist movements of a first joint associated with a right leg of a user and a second joint associated with a left leg of the user; a sensor configured to measure a first joint angle of the first joint and a second joint angle of the second joint; and a controller configured to, generate a walking assist profile based on a previous step of the user, modify the walking assist profile based on the first joint angle and the second joint angle, and control the driver based on the modified walking assist profile.

In some example embodiments, the first joint is a right hip-joint of the user and the second joint is a left hip-joint of the user.

In some example embodiments, the controller is configured to modify the walking assist profile based on a value of at least one of a first joint angular velocity and a second joint angular velocity when the first joint angle is same as the second joint angle, the first joint angular velocity and the second joint angular velocity being angular velocities associated with the first joint and the second joint, respectively.

In some example embodiments, the controller is configured to modify the walking assist profile based on one of the first joint angular velocity and the second joint angular velocity that corresponds to a leg swinging in a gait direction of the user.

In some example embodiments, the controller is configured to modify the walking assist profile such that the first joint angle and the second joint angle gradually change starting from a point in time when the first joint angle is the same as the second joint angle.

In some example embodiments, the controller is configured to determine that a current step of the user has positive work properties in relation to the previous step if one of the first joint angular velocity and the second joint angular velocity is greater than a threshold while the first joint angle is same as the second joint angle.

In some example embodiments, the controller is configured to determine that a current step of the user has negative work properties in relation to the previous step if one of the first joint angular velocity and the second joint angular velocity is less than a threshold while the first joint angle is same as the second joint angle.

In some example embodiments, the walking assist profile indicates an assistance torque applied by the driver to at least one of the first joint and the second joint.

In some example embodiments, the controller is configured to increase at least one of intensity and duration of the assistance torque in the walking assist profile if a current step is determined to have positive work properties in relation to the previous step.

In some example embodiments, the controller is configured to decrease at least one of intensity and duration of the assistance torque in the walking assist profile if a current step of the user is determined to have negative work properties in relation to the previous step.

In some example embodiments, the controller is configured to estimate a first joint angular velocity based on the first joint angle and estimate a second joint angular velocity based on the second joint angle, the first joint angular velocity and the second joint angular velocity being angular velocities associated with the first joint and the second joint, respectively.

Some example embodiments relate to a method of operating a walking assistance apparatus.

In some example embodiments, the method includes generating a walking assist profile based on a previous step of a user; measuring a first joint angle of a first joint associated with a right leg of a user and a second joint angle of a second joint associated with a left leg of the user; modifying the walking assist profile based on the first joint angle and the second joint angle; and controlling a driver to assist movements of the first joint and the second joint based on the modified walking assist profile.

In some example embodiments, the modifying includes modifying the walking assist profile based on a value of at least one of a first joint angular velocity and a second joint angular velocity of the user when the first joint angle is same as the second joint angle, the first joint angular velocity and the second joint angular velocity being angular velocities associated with the first joint and the second joint, respectively.

In some example embodiments, the modifying further includes modifying the walking assist profile such that the first joint angle and the second joint angle gradually change starting from a point in time when the first joint angle is the same as the second joint angle.

In some example embodiments, the method further includes determining that a current step of the user has positive work properties in relation to the previous step if one of the first joint angular velocity and the second joint angular velocity cis greater than a threshold while the first joint angle is same as the second joint angle.

In some example embodiments, the method further includes determining that a current step of the user has negative work properties in relation to the previous step if one of the first joint angular velocity and the second joint angular velocity is less than a threshold while the first joint angle is same as the second joint angle.

In some example embodiments, the walking assist profile indicates an assistance torque applied by the driver to at least one of the first joint and the second joint.

In some example embodiments, the method further includes increasing at least one of intensity and duration of the assistance torque in the walking assist profile if a current step is determined to have positive work properties in relation to the previous step.

In some example embodiments, the method further includes decreasing at least one of intensity and duration of the assistance torque in the walking assist profile if a current step of the user is determined to have negative work properties in relation to the previous step.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
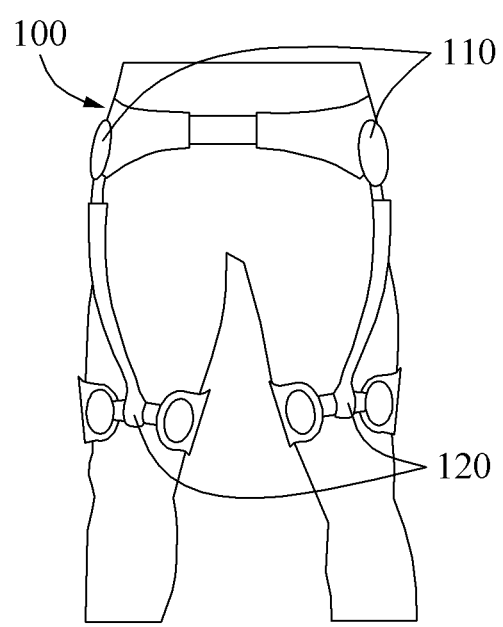
FIG. 1 illustrates an example of a walking assistance apparatus attached to a user.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. Terms, such as those defined in commonly used dictionaries, should be interpreted as having a meaning that is consistent with their meaning in the context of the relevant art and/or this disclosure, and should not be interpreted in an idealized or overly formal sense unless expressly so defined herein.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as one computer processing device; however, one skilled in the art will appreciate that a hardware device may include multiple processing elements and multiple types of processing elements. For example, a hardware device may include multiple processors or a processor and a controller. In addition, other processing configurations are possible, such as parallel processors.

Various example embodiments will now be described more fully with reference to the accompanying drawings in which some example embodiments are shown. In the drawings, the thicknesses of layers and regions are exaggerated for clarity.

FIG. 1 illustrates a walking assistance apparatus 100 attached to a user.

The walking assistance apparatus 100 may assist movements of muscles or joints of a swinging leg and a supporting leg of the user, thereby reducing energy consumption and leading to an appropriate posture while the user is walking. Although FIG. 1 illustrates the walking assistance apparatus 100 as, for example, a hip-type walking assistance apparatus, the walking assistance apparatus 100 is not limited to that type. For example, the walking assistance apparatus 100 may be applicable to, for example, a walking assistance apparatus that supports an entire pelvic limb, a walking assistance apparatus that supports a portion of a pelvic limb, etc. The walking assistance apparatus that supports a portion of a pelvic limb may be applicable to, for example, a walking assistance apparatus that supports up to a knee, and a walking assistance apparatus that supports up to an ankle.

The walking assistance apparatus 100 may include a driver 110 and a transmitter 120. The driver 110 may provide a force assisting a muscle or a joint of the user to assist movements of a right leg and a left leg. The driver 110 may apply an assistance torque, for example, τR and τL, to at least one of a right hip-joint and a left hip-joint, respectively.

The assistance torque provided by the driver 110 may be applied through the transmitter 120 in a direction of pushing or pulling a leg of the user. Forms of the driver 110 and the transmitter 120, parts to which the driver 110 and transmitter 120 are attached, and a type of force applied to the driver 110 and the driver 120 may be appropriately provided based on a type of a walking assistance apparatus.

Figure 2:
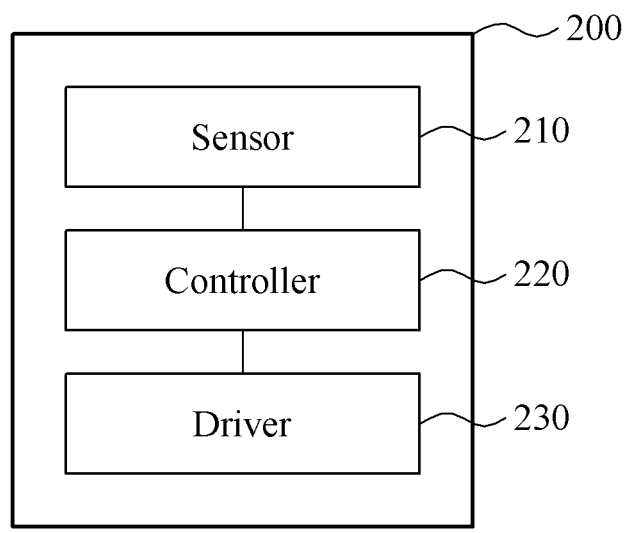
FIG. 2 illustrates an example of a walking assistance apparatus.

FIG. 2 illustrates a walking assistance apparatus 200. The walking assistance apparatus 200 may include a sensor 210, a controller 220, and a driver 230.

The sensor 210 may measure joint angles qR and qL of right and left legs of a user. The sensor 210 may measure angles of, for example, hip-joints, knee-joints, and ankle-joints of the right and left legs of the user. The sensor 210 may separately measure joint angular velocities qR' and qL' of the right and left legs of the user or estimate the joint angular velocities qR' and qL' based on the joint angles qR and qL. Also, the sensor 210 may separately measure joint angular accelerations qR" and qL" of the right and left legs of the user or estimate the joint angular accelerations qR" and qL" based on the joint angular velocities qR' and qL'.

The controller 220 may include a memory and a processor (not shown).

The memory may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM).

The processor may be implemented by at least one semiconductor chip disposed on a printed circuit board. The processor may be an arithmetic logic unit, a digital signal processor, a microcomputer, a field programmable array, a programmable logic unit, a microprocessor or any other device capable of responding to and executing instructions in a defined manner.

Figure 6:
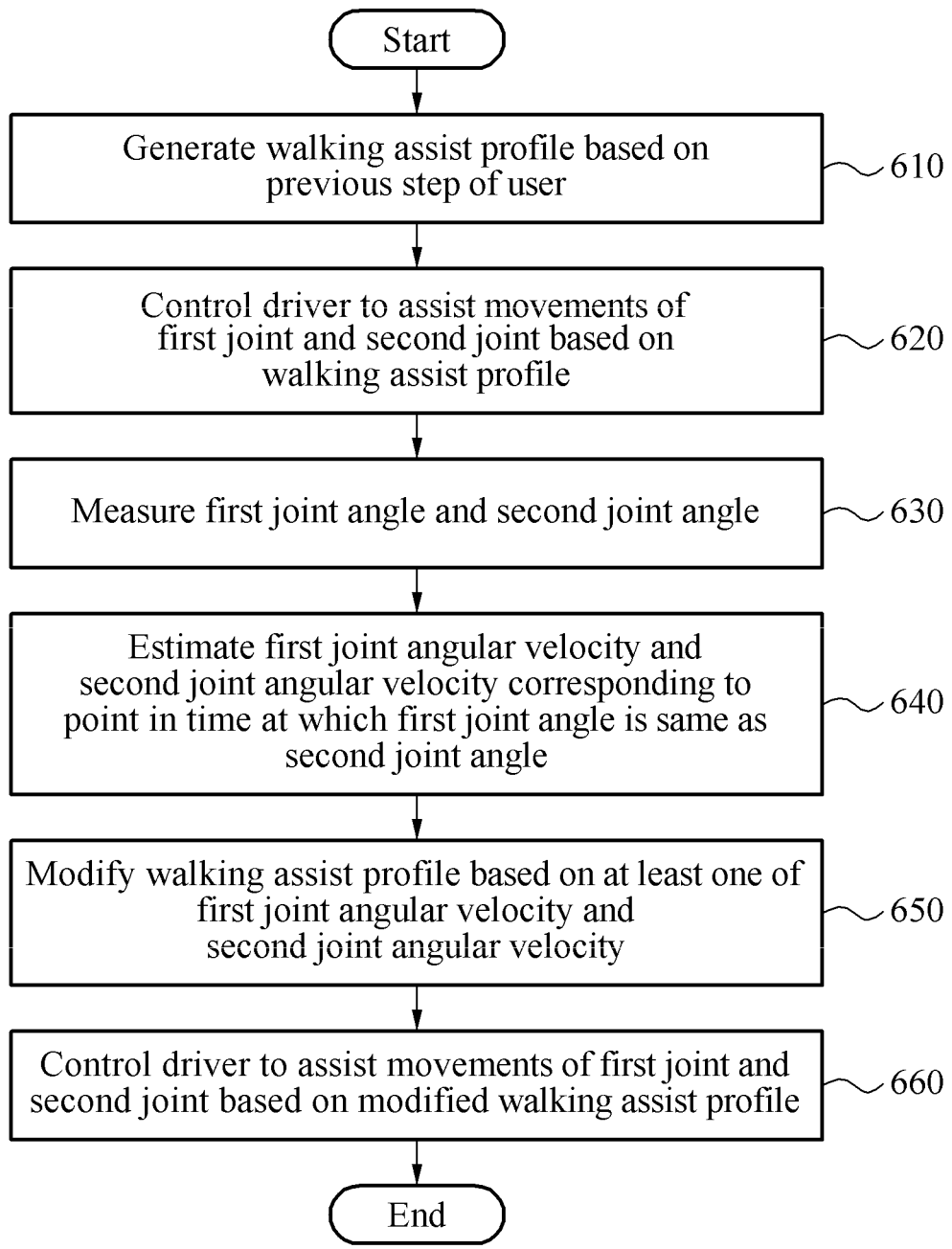
FIG. 6 is a flowchart illustrating an example of a walking assistance apparatus operation method.
Figure 7:
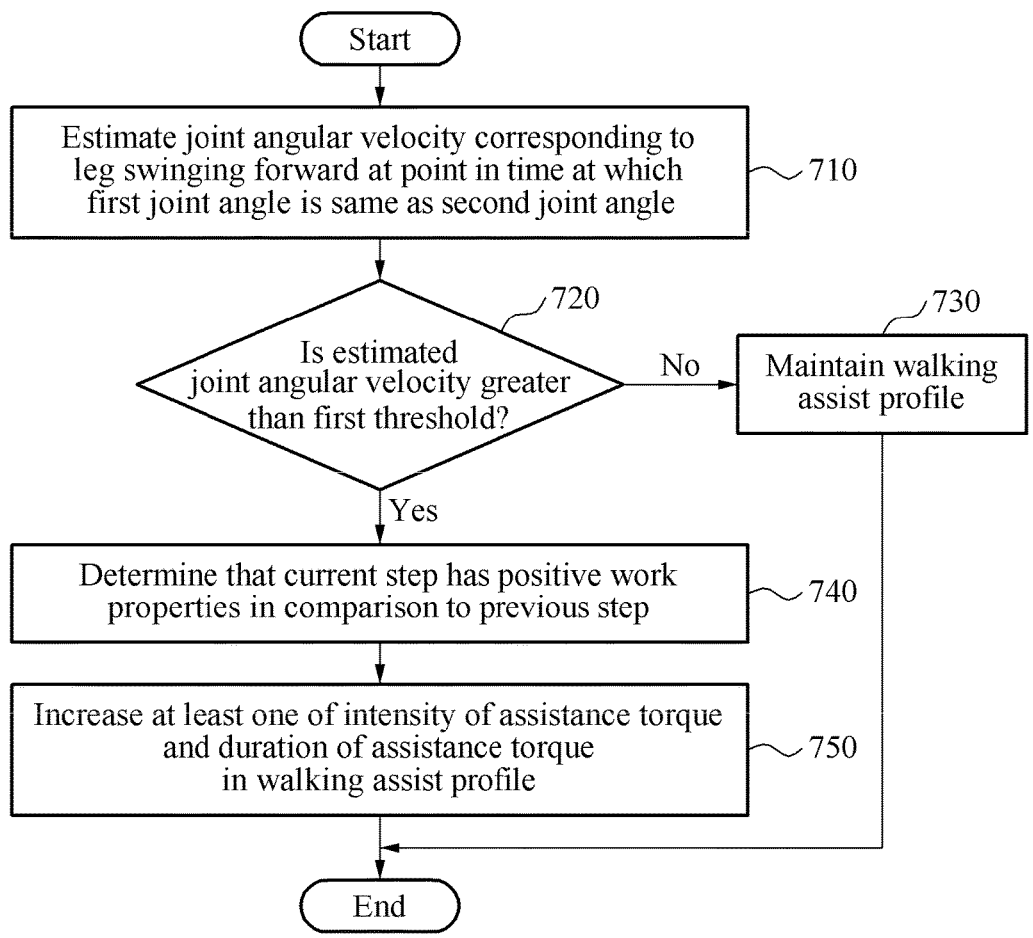
FIG. 7 is a flowchart illustrating another example of a walking assistance apparatus operation method.
Figure 9:
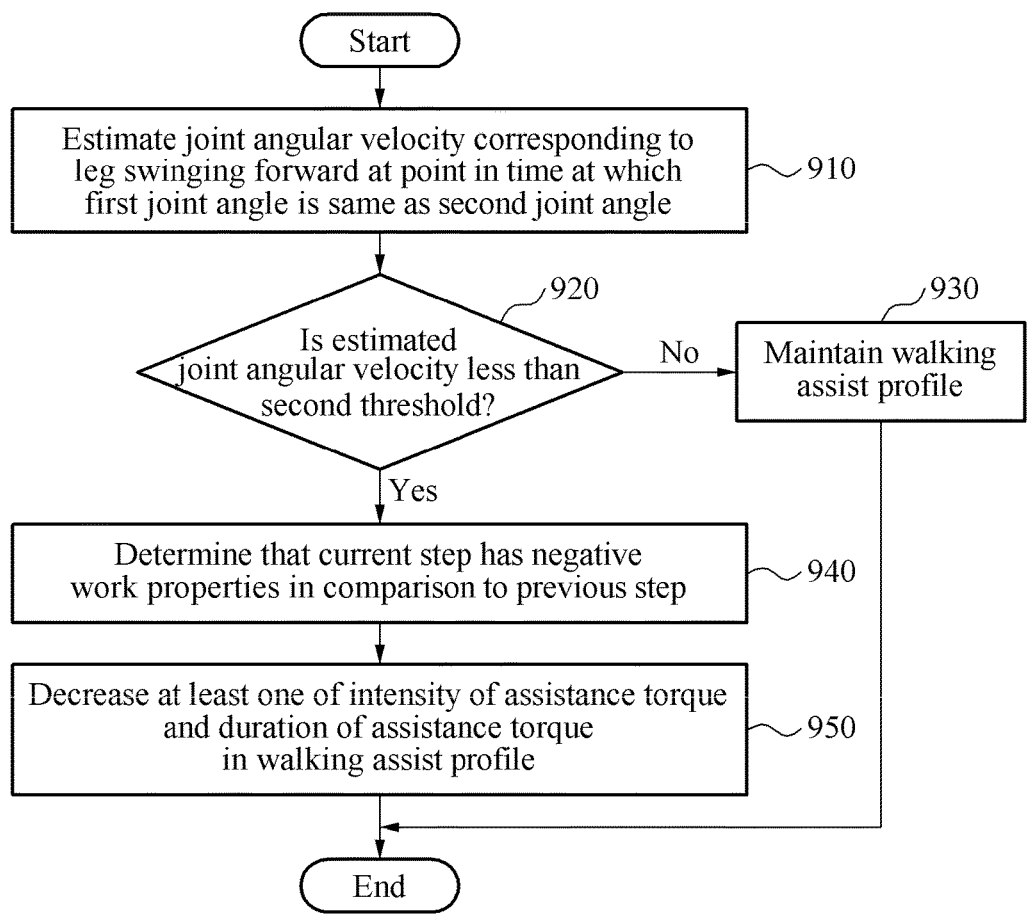
FIG. 9 is a flowchart illustrating still another example of a walking assistance apparatus operation method.

The processor may be programmed with instructions that configure the processor into a special purpose computer to perform the operations illustrated in FIGS. 6, 7 and 9 to perform feed forward control by modifying a walking assist profile to increase or decrease an assistance torque applied to the right leg and the left leg of the user based on whether a joint angle indicates that the user is performing positive or negative work thereon. Therefore the processor may improve the functioning of the controller 220 itself by modifying the walking assist profile to perform the natural gait assistance when the gait style of the user suddenly changes.

The controller 220 may improve gait safety through a feed forward control based on information on a previous step of the user from information received from the sensor 210. As an example, the controller 220 may generate a walking assist profile to be applied to the user by the walking assistance apparatus 200, based on the information on the previous step of the user. The information on the previous step of the user may be at least one of the joint angles, the joint angular velocities, and the joint angular accelerations of the right and left legs of the user. The walking assist profile may include a profile of a force applied to assist a joint or a muscle of the user.

The controller 220 may detect a change in a gait style of the user based on information corresponding to a point in time satisfying a predetermined (or, alternatively, a desired) condition from the information received from the sensor 210. As an example, when the user suddenly suspends walking or reduces speed while walking, the controller 220 may determine that a current step of the user has negative work properties in comparison to the previous step. As another example, when the user suddenly increases speed while walking, the controller 220 may determine that the current step of the user has positive work properties in comparison to the previous step.

Information used by the controller 220 to detect the change in the gait style of the user may be information corresponding to a point in time at which the joint angle of the right leg and the joint angle of the left leg cross each other. As an example, the used information may be at least one of the joint angular velocities qR' and qL' corresponding to a point in time at which the joint angle qR of the right leg is the same as the joint angle qL of the left leg. For example, the controller 220 may use a joint angular velocity corresponding to a leg swinging in a gait direction of the user between the joint angular velocities of the right and left legs of the user. Alternatively, the controller 220 may use information corresponding to a point in time at which a difference between the joint angle of the right leg and the joint angle of the left leg satisfy a predetermined (or, alternatively, a desired) value during the walking.

The controller 220 may modify the walking assist profile being applied to the current step by applying the change in the gait style of the user. When the current step is radically changed in comparison to the previous step, the user may conventionally experience inconvenience due to a gait assistance provided based on the walking assist profile generated using information on the previous step. As an example, when the user suddenly reduces speed, the reduced speed may not be applied to the walking assist profile applied in advance and thus, the same gait assistance as that of the previous step may be provided to a user through a control based on the walking assist profile.

In contrast, in one or more example embodiments, to compensate for a difference generated in the gait assistance currently provided due to the change in the gait style of the user, the controller 220 may modify the walking assist profile by applying the change in the gait style of the user.

The driver 230 may provide a force assisting a joint or a muscle of the user to assist movements of the right and left legs of the user. The driver 230 may apply an assistance torque, for example, τR and τL, to at least one of a right hip-joint and a left hip-joint of the user. A form of the driver 230, a part to which the driver 230 is attached, and a type of force applied to the driver 230 may be appropriately provided based on a type of a walking assistance apparatus.

Figure 3:
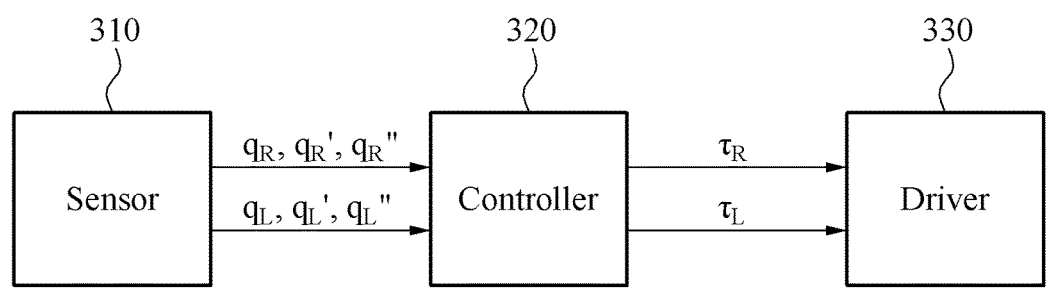
FIG. 3 illustrates another example of a walking assistance apparatus.

FIG. 3 illustrates an example of a walking assistance apparatus. The walking assistance apparatus may include a sensor 310, a controller 320, and a driver 330.

The sensor 310 may transmit at least one of joint angles qR and qL, joint angular velocities qR' and qL', and joint angular accelerations qR" and qL" of right and left legs of a user to the controller 320. The joint angular velocities qR' and qL', and the joint angular accelerations qR" and qL" may be separately measured or estimated based on the joint angles qR and qL. After the sensor 310 estimates the joint angular velocities qR' and qL', and the joint angular accelerations qR" and qL", the joint angular velocities qR' and qL', and the joint angular accelerations qR" and qL" may be transmitted to the controller 320 or estimated by the controller 320.

The controller 320 may transmit, to the driver 330, a force assisting a joint or a muscle of the user to assist movements of the right and left legs of the user, based on at least one of the joint angles qR and qL, the joint angular velocities qR' and qL', and the joint angular accelerations qR" and qL" of the right and left legs of the user. The controller 320 may transmit, to the driver 330, assistance torques τR and τL to be applied to a right hip-joint and a left hip-joint of the user.

The driver 330 may provide the force assisting the joint or the muscle of the user to assist the movements of the right and left legs of the user. The driver 330 may apply the assistance torque, for example, τR and τL, to at least one of the right hip-joint and the left hip-joint of the user. A form of the driver 330 and, a part to which the driver 330 is attached, and a type of force applied to the driver 330 may be appropriately provided based on a type of a walking assistance apparatus.

Figure 4:
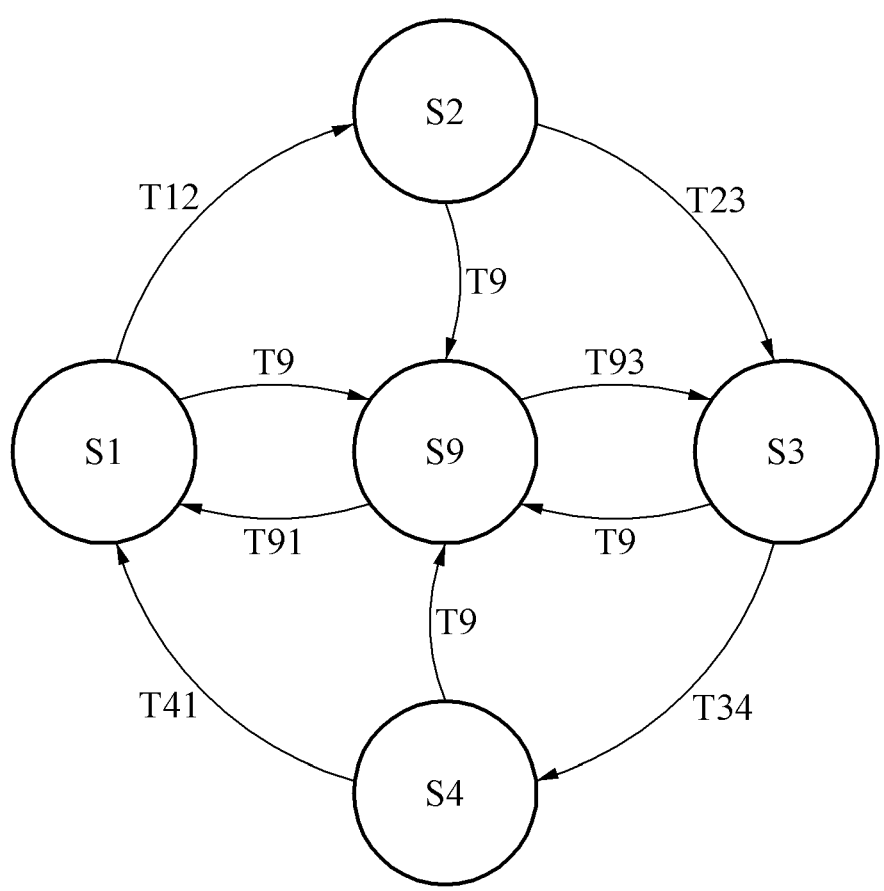
FIG. 4 illustrates an example of a finite state machine (FSM) in a walking assistance apparatus.

FIG. 4 illustrates an example of a finite state machine (FSM) in a walking assistance apparatus. The FSM of the walking assistance apparatus may include gait states S1, S2, S3, S4, and S9 of a user. A gait state may be transitioned based on a transition condition defined among gait states, for example, in advance.

In the gait state S1, a right leg may be landing on the ground and a left leg may start swinging. Conditions T41 and T91 for transition to the gait state S1 may be an event in which the right leg stops swinging.

In the gait state S2, the right leg may be in a stance state in which the user is standing on the right leg while the left leg is swinging. Condition T12 for transition to the gait state S2 may be an event in which the right leg and the swinging left leg cross each other.

In the gait state S3, the left leg may be landing on the ground and the right leg may start swinging. Conditions T23 and T93 for transition to the gait state S3 may be an event in which the left leg stops swinging.

In the gait state S4, the left leg may be in a stance state in which the user is standing on the left leg while the right leg is swinging. Condition T34 for transition to the gait state S4 may be an event in which the left leg and the swinging right leg cross each other.

The gait state S9 may be defined as an exceptional state. A condition for transition to the gait state S9 may be, for example, a case in which a difference in joint angle between the right leg and the left leg is greater than a threshold, and a case in which a predetermined (or, alternatively, a desired) time elapses without transitioning from a predetermined (or, alternatively, a desired) state to another state. In terms of gait states of the FSM, all gait states may be transitioned to, an exceptional state, the gait state S9, whereas the gait state S9 may be transitioned to only the gait states S1 and S3 in which the user starts taking a step.

Figure 5:
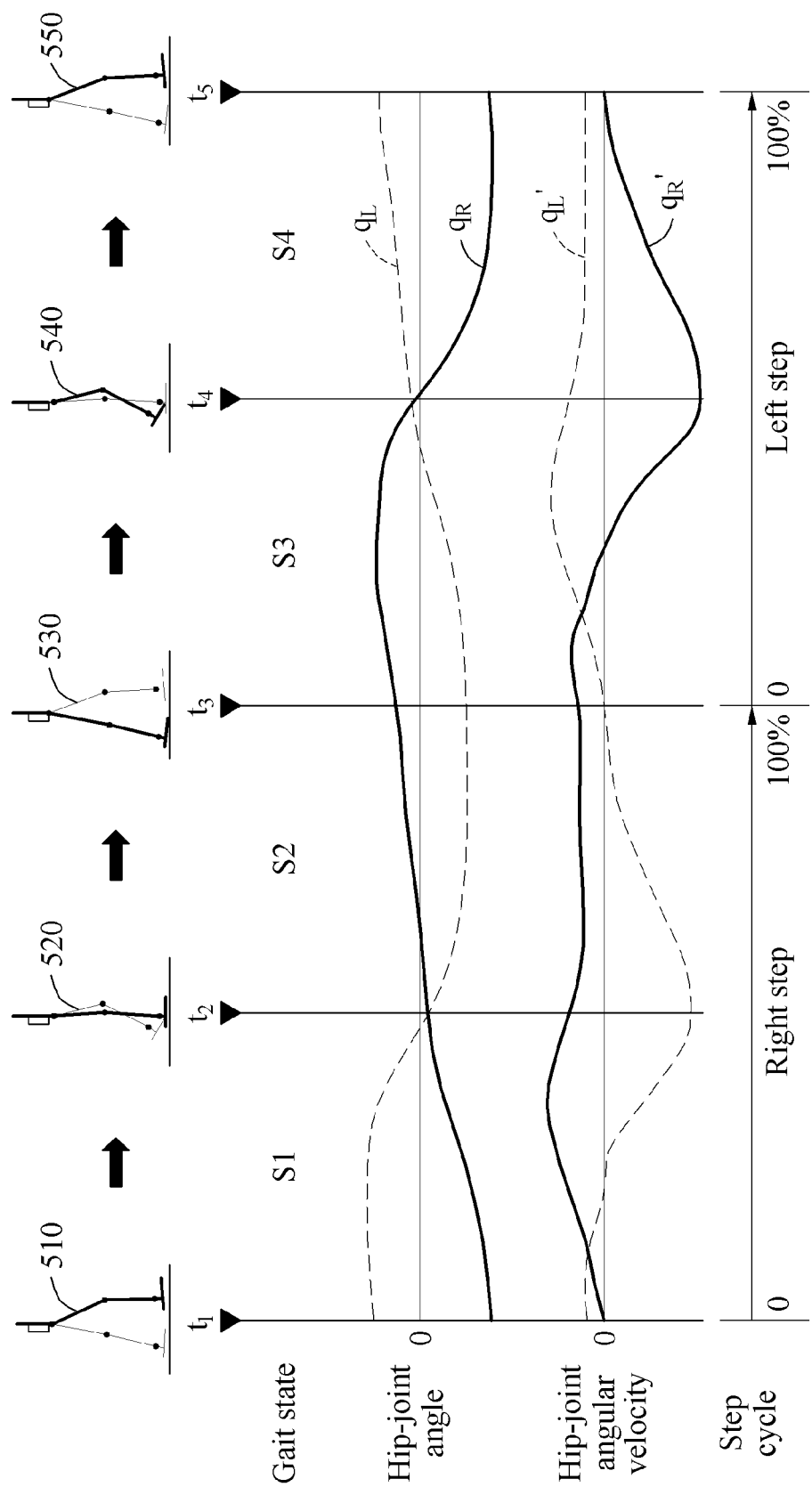
FIG. 5 illustrates an example of a hip-joint angle, a hip-joint angular velocity, and a transition of gait states included in an FSM.

FIG. 5 illustrates an example of a hip-joint angle, a hip-joint angular velocity, and a transition of gait states included in an FSM. FIG. 5 illustrates a profile of a hip-joint angle, a hip-joint angular velocity, and transition among states S1, S2, S3, and S4 included in an FSM. Referring to FIG. 5, in events 510, 520, 530, 540, and 550 occurring during a gait state, a right leg of a user may be indicated by a bold-solid line and a left leg of the user may be indicated by a solid line.

A gait state may be transitioned to the state S1 at an occurrence point in time t1 of an event 510 in which the right leg stops swinging. For example, the FSM may detect a point in time at which a hip-joint angular velocity qR' of the right leg is 0, as the occurrence point in time t1 of the event 510.

The gait state may be transitioned to the state S2 at an occurrence point in time t2 of an event 520 in which the swinging left leg and the right leg cross each other. For example, the FSM may detect a point in time at which hip-joint angles qR and qL of the right leg and the swinging left leg cross each other, as the occurrence point in time t2 of the event 520.

The gait state may be transitioned to the state S3 at an occurrence point in time t3 of an event 530 in which the left leg stops swinging. For example, the FSM may detect a point in time at which a hip-joint angular velocity qL' of the left leg is 0, as the occurrence point in time t3 of the event 530.

The gait state may be transitioned to the state S4 at an occurrence point in time t4 of an event 540 in which the swinging right leg and the left leg cross each other. For example, the FSM may detect a point in time at which the hip-joint angles qR and qL of the swinging right leg and the left leg cross each other, as the occurrence point in time t4 of the event 540.

As described above, the transition among the states S1, S2, S3, and S4 may be performed at the point in time at which the hip-joint angular velocity of the right leg or the left leg is 0, or at the point in time at which the hip-joint angles qR and qL cross each other.

When the gait of the user is maintained without radical change in a gait style, the gait state may be transitioned to the state S1 at an occurrence point in time t5 of an event 550 in which the right leg stops swinging, and the transition among the states S1, S2, S3, and S4 may be repetitively performed in sequence. In this example, a walking assistance apparatus may perform a natural gait assistance based on the walking assist profile generated based on information on a previous step of the user. In contrast, when the gait style of the current step is significantly changed from that of the previous step, the controller 220, 320 may modify the walking assist profile to perform the natural gait assistance.

FIG. 6 is a flowchart illustrating an example of a walking assistance apparatus operation method. The walking assistance apparatus operation method of FIG. 6 may be performed by, for example, the walking assistance apparatus 200 of FIG. 2.

In operation 610, the walking assistance apparatus 200 may generate a walking assist profile based on a previous step of a user. For example, the walking assistance apparatus 200 may generate the walking assist profile for a feed forward control based on information on the previous step of the user. The information on the previous step of the user may be at least one of joint angles, joint angular velocities, and joint angular accelerations of right and left legs of the user. The walking assist profile may include a profile of a force applied to assist a joint or a muscle of the user.

In operation 620, the walking assistance apparatus 200 may control a driver to assist a first joint related to the right leg and a second joint related to the left leg based on the walking assist profile. For example, the first joint may be a right hip-joint of the user and the second joint may be a left hip-joint of the user.

In operation 630, the walking assistance apparatus 200 may measure a first joint angle and a second joint angle. The walking assistance apparatus 200 may measure the first joint angle and the second joint angle via a sensor included in the walking assistance apparatus 200. The walking assistance apparatus 200 may include various types of sensors. In some example embodiments, the walking assistance apparatus 200 may include only a joint angle sensor to reduce weight, complexity, and power consumption.

In operation 640, the walking assistance apparatus 200 may estimate a first joint angular velocity and a second joint angular velocity corresponding to a point in time at which the first joint angle is the same as the second joint angle. When the first joint is the right hip-joint of the user and the second joint is the left hip-joint of the user, the point in time at which the first joint angle is the same as the second joint angle may be a point in time at which both legs of the user cross each other during a gait state. The point in time at which both legs of the user cross each other may be detected, for example, in a state in which the user is standing with the right leg and swinging the left leg and a state in which the user is standing with the left leg and swinging the right leg.

In operation 650, the walking assistance apparatus 200 may modify the walking assist profile based on at least one of the first joint angular velocity and the second joint angular velocity. The walking assistance apparatus 200 may modify the walking assist profile based on a joint angular velocity corresponding to a leg swinging in a gait direction of the user between the first joint angular velocity and the second joint angular velocity. As an example, when a user is standing with the right leg and swinging the left leg, the walking assist profile may be modified based on a joint angular velocity corresponding to the left leg. To compensate for a difference between a gait assistance being currently applied and a change in a gait style of the user, the walking assistance apparatus 200 may modify the walking assist profile based on a result of comparison between the joint angular velocity corresponding to the leg swinging in the gait direction of the user and at least one threshold. Descriptions related to an example of modifying the walking assist profile will be also provided with reference to FIGS. 7 through 10.

In operation 660, the walking assistance apparatus 200 may control the driver to assist movements of the first joint and the second joint based on the modified walking assist profile. Since a change in a gait style of the current step is applied to the modified walking assist profile, the walking assistance apparatus 200 may provide the gait assistance such that a gait is naturally performed when the user suddenly increases or decreases speed during the gait state.

FIG. 7 is a flowchart illustrating another example of an operation method of a walking assistance apparatus.

Referring to FIGS. 2, 6 and 7, the walking assistance apparatus operation method of FIG. 7 may indicate an example of operation 650 described with reference to FIG. 6. The walking assistance apparatus operation method of FIG. 7 may be performed by, for example, the walking assistance apparatus 200 of FIG. 2.

In operation 710, the walking assistance apparatus 200 may estimate a joint angular velocity corresponding to a leg swinging forward at a point in time at which a first joint angle related to a right leg of a user is the same as a second joint angle related to a left leg of the user. Alternatively, when a gait direction of the user is a backward direction, the walking assistance apparatus 200 may estimate a joint angular velocity corresponding to a leg swinging backward. When a first joint angle and a second joint angle are a right hip-joint angle and a left hip-joint angle, the point in time at which the first joint angle is the same as the second joint angle may be a point in time at which both legs of the user cross each other during a gait.

In operation 720, the walking assistance apparatus 200 may determine whether the estimated joint angular velocity is greater than a first threshold. When the estimated joint angular velocity is less than or equal to the first threshold, the walking assistance apparatus 200 may determine that the current step of the user does not include the change in the gait style in comparison to the previous step. In this example, operation 730 may be performed. Conversely, when the estimated joint angular velocity is greater than the first threshold, operation 740 may be performed.

In operation 730, the walking assistance apparatus 200 may maintain the walking assist profile generated based on information on the previous step of the user. Since the current step does not include the change in the gait style in comparison to the previous step, a gait may be naturally performed based on the gait assistance to which the maintained walking assist profile is applied.

In operation 740, the walking assistance apparatus 200 may determine that the current step of the user has positive work properties in comparison to the previous step. For example, through a comparison between the estimated angular velocity and the first threshold, a speed increasing in the current step when compared to the previous step may be verified. In this example, the walking assistance apparatus 200 may perform operation 750 to apply the change in the gait style to the walking assist profile.

In operation 750, the walking assistance apparatus 200 may increase at least one of an intensity of an assistance torque and duration of the assistance torque in the walking assist profile. Since the speed increasing in the current step when compared to the previous step is verified, a natural gait assistance corresponding to the change in the gait style may be performed through an increase in a force applied to the gait assistance. A type of force applied to the gait assistance may vary based on a type of the walking assistance apparatus 200.

Figure 8A:
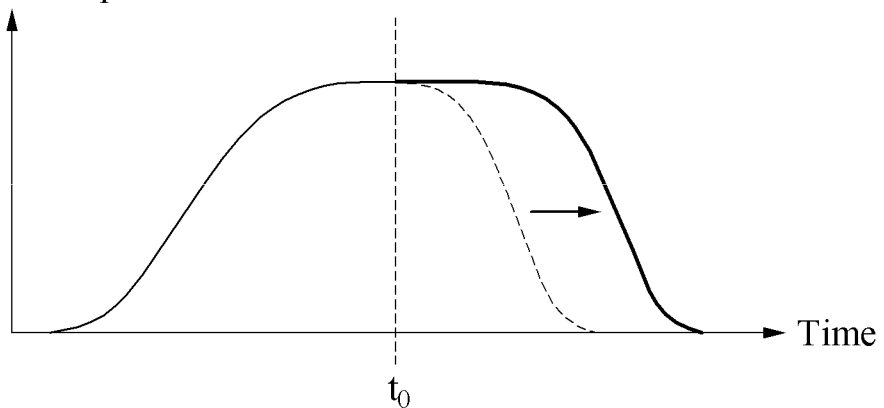
FIGS. 8A through 8C are graphs illustrating an example of an assistance torque controlled by a walking assistance apparatus.
Figure 8B:
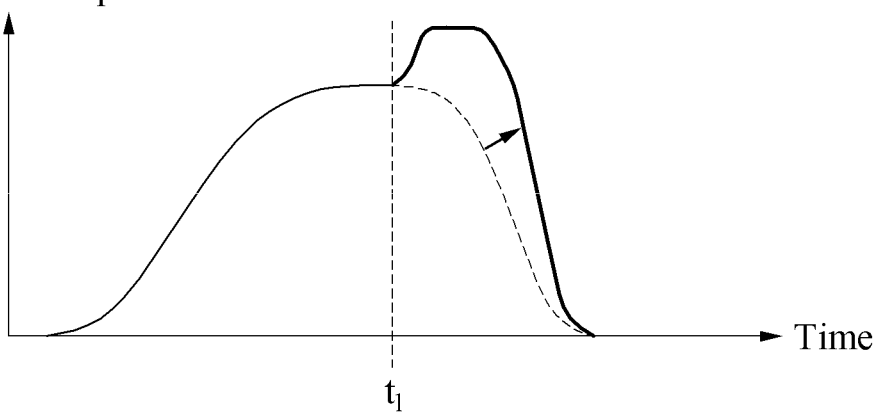
Figure 8C:
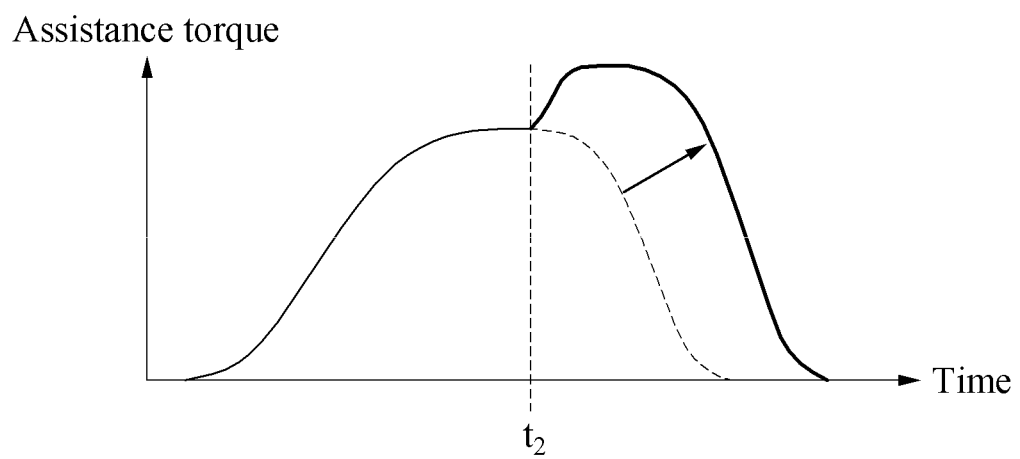

FIGS. 8A through 8C are graphs illustrating an example of an assistance torque controlled by a walking assistance apparatus.

Referring to FIGS. 8A to 8C, a reference time at which the walking assistance apparatus 200 may detect a change in a gait style of a user may be indicated by t0. When a current step of a user is determined to have positive work properties in comparison to a previous step based on information on a joint of the user corresponding to the reference time t0, the walking assistance apparatus 200 may increase at least one of an intensity of an assistance torque and duration of the assistance torque in the walking assist profile.

FIG. 8A illustrates an example of increasing the duration of the assistance torque in the walking assistance apparatus. FIG. 8B illustrates an example of increasing the intensity of the assistance torque in the walking assistance apparatus. FIG. 8C illustrates an example of increasing the intensity and the duration of the assistance torque in the walking assistance apparatus. To prevent the user from experiencing inconvenience due to a change in the assistance torque being applied to the user, the walking assistance apparatus 200 may modify the walking assist profile to prevent a radical change in the assistance torque and allow the assistance torque to be changed gradually.

FIG. 9 is a flowchart illustrating still another example of a walking assistance apparatus operation method.

Referring to FIGS. 6 and 9, the walking assistance apparatus operation method of FIG. 9 may indicate an example of operation 650 described with reference to FIG. 6. The walking assistance apparatus operation method of FIG. 9 may be performed by, for example, the walking assistance apparatus 200 of FIG. 9.

In operation 910, the walking assistance apparatus 200 may estimate a joint angular velocity corresponding to a leg swinging forward at a point in time at which a first joint angle related to a right leg of a user is the same as a second joint angle related to a left leg of the user. Alternatively, when a gait direction of the user is a backward direction, the walking assistance apparatus 200 may estimate a joint angular velocity corresponding to a leg swinging backward. When a first joint angle and a second joint angle are a right hip-joint angle and a left hip-joint angle, the point in time at which the first joint angle is the same as the second joint angle may be a point in time at which both legs of the user cross each other during a gait state.

In operation 920, the walking assistance apparatus 200 may determine whether the estimated joint angular velocity is less than a second threshold. When the estimated joint angular velocity is greater than or equal to the second threshold, the walking assistance apparatus operation method may determine that the current step of the user does not include the change in the gait style in comparison to the previous step. In this example, operation 930 may be performed. Conversely, when the estimated joint angular velocity is less than the second threshold, operation 940 may be performed.

In operation 930, the walking assistance apparatus 200 may maintain the walking assist profile generated based on information on the previous step of the user. Since the current step does not include the change in the gait style in comparison to the previous step, a gait may be naturally performed based on the gait assistance to which the maintained walking assist profile is applied.

In operation 940, the walking assistance apparatus 200 may determine that the current step of the user has negative work properties in comparison to the previous step. For example, through a comparison between the estimated angular velocity and the second threshold, a speed decreasing in the current step when compared to the previous step may be verified. In this example, the walking assistance apparatus 200 may perform operation 950 to apply the change in the gait style to the walking assist profile.

In operation 950, the walking assistance apparatus 200 may decrease at least one of an intensity of an assistance torque and duration of the assistance torque in the walking assist profile. Since the speed decreasing in the current step when compared to the previous step is verified, a natural gait assistance corresponding to the change in the gait style may be performed through a decrease in a force applied to the gait assistance. A type of force applied to the gait assistance may vary based on a type of the walking assistance apparatus 200.

The walking assistance apparatus 200 may perform operations 720 and 920 at a same time, such that if the walking assistance apparatus 200 determines, in operation 720, that the joint angular velocity is greater than the first threshold, the walking assistance apparatus 200 may proceed with operation 740, and if the walking assistance apparatus 200 determines, in operation 920, that the joint angular velocity is less than the second threshold, the walking assistance apparatus 200 may proceed with operation 940.

Figure 10A:
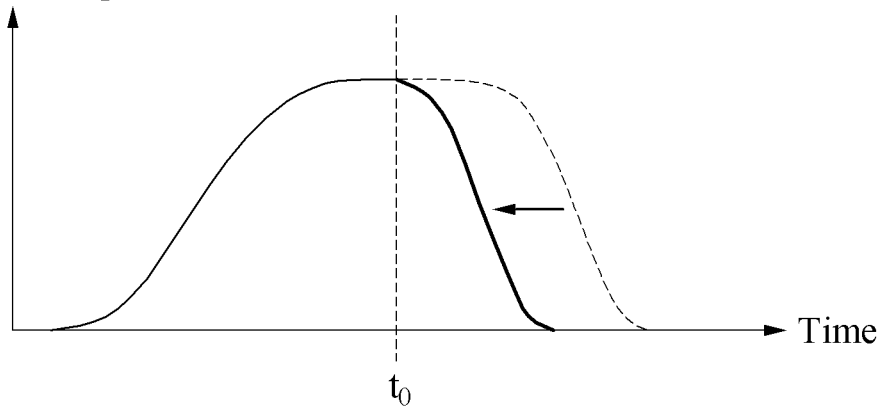
FIGS. 10A through 10C are graphs illustrating another example of an assistance torque controlled by a walking assistance apparatus.
Figure 10B:
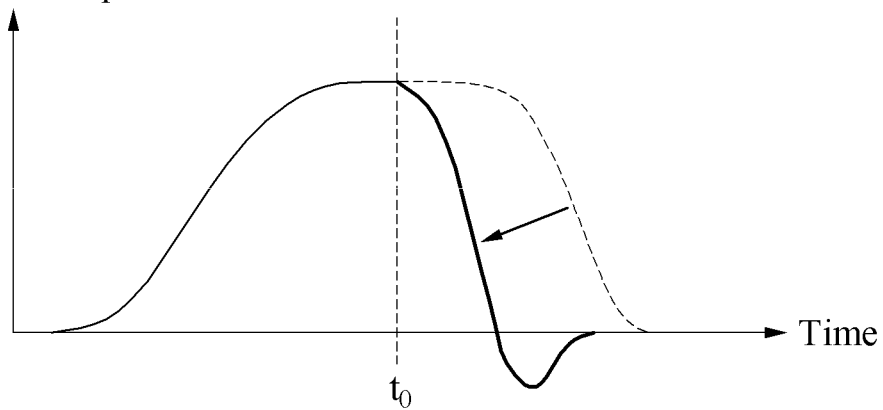
Figure 10C:
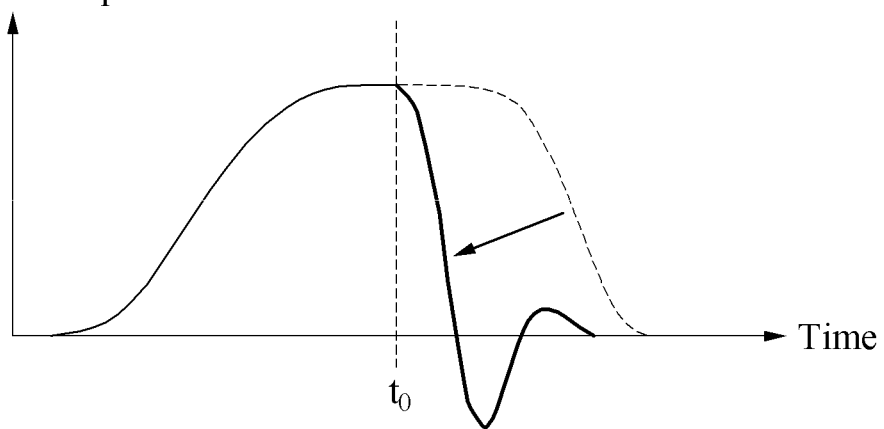

FIGS. 10A through 10C are graphs illustrating another example of an assistance torque controlled by a walking assistance apparatus.

Referring to FIGS. 10A to 10C, a reference time at which a change in a gait style of a user is detected by the walking assistance apparatus 200 may be indicated by t0. When a current step of a user is determined to have negative work properties in comparison to a previous step based on information on a joint of the user corresponding to the reference time t0, the walking assistance apparatus may decrease at least one of an intensity of an assistance torque and duration of the assistance torque in the walking assist profile.

FIG. 10A illustrates an example of decreasing the duration of the assistance torque in the walking assistance apparatus 200. FIGS. 10B and 10C illustrate an example of decreasing the intensity and the duration of the assistance torque in the walking assistance apparatus 200 and reversing a direction in which the assistance torque is applied in a (desired, or alternatively, a predetermined) interval. To prevent the user from experiencing inconvenience due to a change in the assistance torque being applied to the user, walking assistance apparatus 200 may modify the walking assist profile to prevent a radical change in the assistance torque and allow the assistance torque to be changed gradually.

Figure 11:
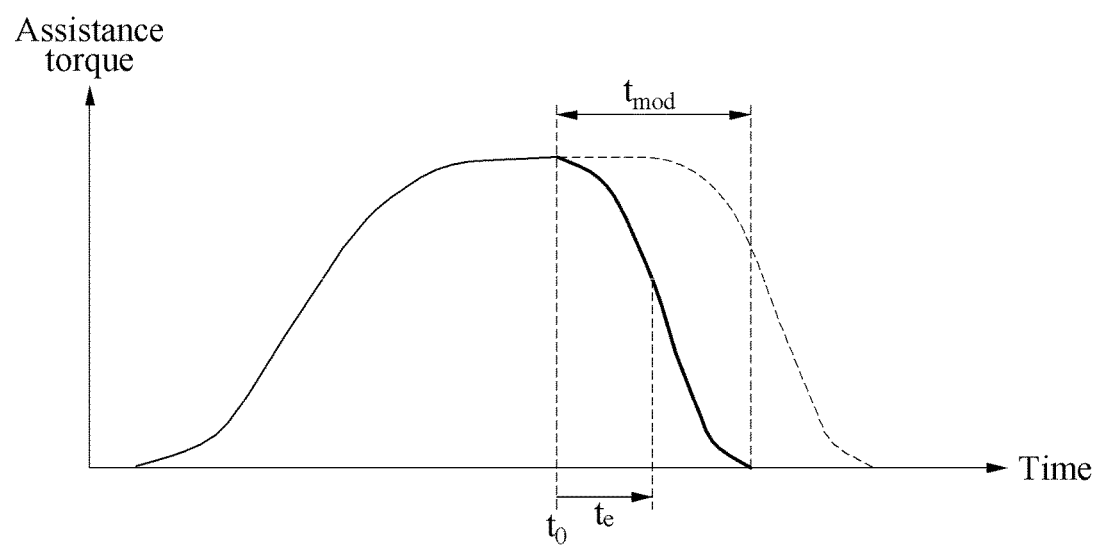
FIG. 11 is a graph illustrating still another example of an assistance torque controlled by a walking assistance apparatus.

FIG. 11 is a graph illustrating still another example of an assistance torque controlled by a walking assistance apparatus.

Referring to FIG. 11, a reference time at which the walking assistance apparatus 200 may detect a change in a gait style of a user may be indicated by t0. The walking assistance apparatus 200 may increase or decrease an assistance torque of the walking assist profile e based on information on a joint of the user corresponding to the reference time t0. Here, a period of time tmod during which the assistance torque reaches a target value, starting from a current value may be defined to prevent a radical change in the assistance torque and allow the assistance torque to be changed gradually in the walking assist profile. For example, the walking assistance apparatus 200 may control an assistance torque profile not to be radically changed to reach the target value and gradually changed during the period of time tmod determined in advance by adding time te. As such, the walking assistance apparatus 200 may perform a natural gait assistance corresponding to the change in the gait style of the user, and prevent the user from experiencing inconvenience due to the modified walking assist profile.

Figure 12:
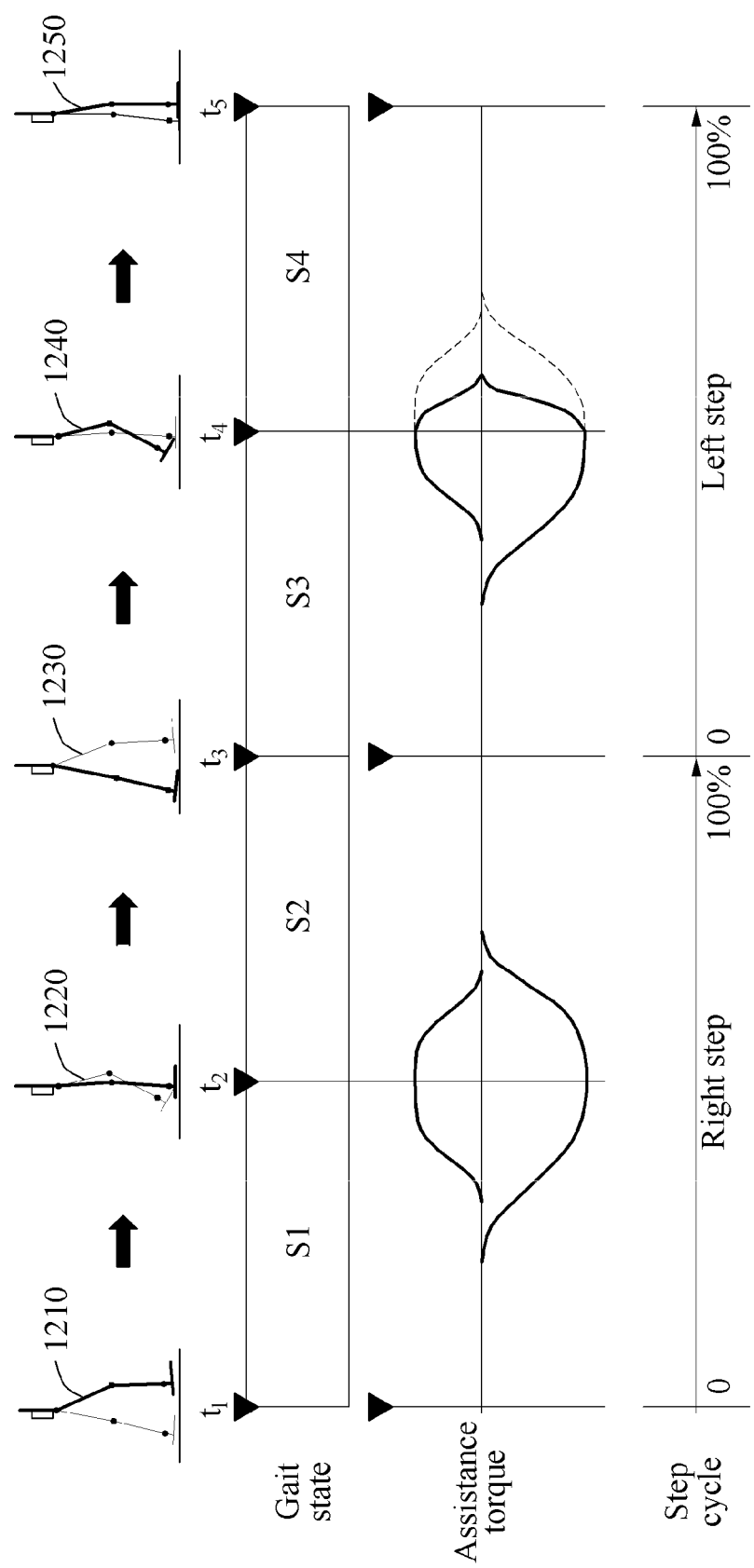
FIG. 12 illustrates an example of an assistance torque and a transition of gait states included in an FSM.

FIG. 12 illustrates an example of an assistance torque and a transition of gait states included in an FSM.

Referring to FIG. 12, FIG. 12 illustrates a profile of an assistance torque and transition among states S1, S2, S3, and S4 included in an FSM. In events 1210, 1220, 1230, 1240, and 1250 occurring during a gait state, a right leg of a user may be indicated by a bold-solid line and a left leg of the user may be indicated by a solid line.

In the states S1 and S2 in which the right step is being taken, it is assumed that a current step of the user does not include a radical change in a gait style when compared to a previous step. In this example, a walking assist profile may be applied without change as illustrated in FIG. 12.

In the states S3 and S4 in which the left step is being taken, the current step of the user may be determined to have negative work properties when compared to the previous step. In this example, the walking assistance apparatus 200 may modify a walking assist profile to reduce an assistance torque applied to the right leg and the left leg of the user. As such, when a gait style of the current step is remarkably changed from the previous step, the walking assistance apparatus 200 may modify the walking assist profile to perform a natural gait assistance such that, for example, when the user applies negative work to stop early, the event 1250 is different from the event 550.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciate that a processing device may include multiple processing elements and multiple types of processing elements. For example, a processing device may include multiple processors or a processor and a controller. In addition, different processing configurations are possible, such as parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A walking assistance apparatus comprising:
   a driver configured to assist movements of a first joint associated with a right leg of a user and a second joint associated with a left leg of the user;
   a sensor configured to measure a first joint angle of the first joint and a second joint angle of the second joint; and
   a controller configured to,
   generate a walking assist profile based on a previous step of the user,
   modify the walking assist profile based on the first joint angle and the second joint angle by,
      determining a cross point in a gait cycle of the user where the first joint angle is same as the second joint angle, based on the first joint angle and the second joint angle,
      comparing a joint angular velocity, at the cross point in the gait cycle, corresponding to a leg swinging in a gait direction of the user with a threshold to determine whether a current step of the user has positive work properties or negative work properties in relation to the previous step, and
      modifying the walking assist profile by selectively increasing or decreasing at least one of intensity and duration of an assistance torque in the walking assist profile such that the controller increases the at least one of intensity and duration of the assistance torque in response to the current step of the user having the positive work properties in relation to the previous step and decreases the at least one of intensity and duration of the assistance torque in response to the current step of the user having the negative work properties in relation to the previous step, and
   control the driver based on the modified walking assist profile.

2. The walking assistance apparatus of claim 1, wherein the first joint is a right hip joint of the user and the second joint is a left hip-joint of the user.

3. The walking assistance apparatus of claim 1, wherein the controller is configured to modify the walking assist profile based on a value of at least one of a first joint angular velocity and a second joint angular velocity when the first joint angle is same as the second joint angle, the first joint angular velocity and the second joint angular velocity being angular velocities associated with the first joint and the second joint, respectively.

4. The walking assistance apparatus of claim 3, wherein the controller is configured to modify the walking assist profile based on one of the first joint angular velocity and the second joint angular velocity that corresponds to the leg swinging in the gait direction of the user.

5. The walking assistance apparatus of claim 3, wherein the controller is configured to modify the walking assist profile such that the first joint angle and the second joint angle gradually change starting from a point in time when the first joint angle is the same as the second joint angle.

6. The walking assistance apparatus of claim 3, wherein the controller is configured to determine that the current step of the user has the positive work properties in relation to the previous step if one of the first joint angular velocity and the second joint angular velocity is greater than the threshold while the first joint angle is same as the second joint angle.

7. The walking assistance apparatus of claim 3, wherein the controller is configured to determine that the current step of the user has the negative work properties in relation to the previous step if one of the first joint angular velocity and the second joint angular velocity is less than the threshold while the first joint angle is same as the second joint angle.

8. The walking assistance apparatus of claim 1, wherein the walking assist profile indicates the assistance torque applied by the driver to at least one of the first joint and the second joint.

9. The walking assistance apparatus of claim 1, wherein the controller is configured to estimate a first joint angular velocity based on the first joint angle and estimate a second joint angular velocity based on the second joint angle, the first joint angular velocity and the second joint angular velocity being angular velocities associated with the first joint and the second joint, respectively.

10. A method of operating a walking assistance apparatus, the method comprising:
   generating a walking assist profile based on a previous step of a user;
   measuring a first joint angle of a first joint associated with a right leg of the user and a second joint angle of a second joint associated with a left leg of the user;
   modifying the walking assist profile based on the first joint angle and the second joint angle by,
      determining a cross point in a gait cycle of the user where the first joint angle is same as the second joint angle, based on the first joint angle and the second joint angle,
      comparing a joint angular velocity, at the cross point in the gait cycle, corresponding to a leg swinging in a gait direction of the user with a threshold to determine whether a current step of the user has positive work properties or negative work properties in relation to the previous step, and
      modifying the walking assist profile by selectively increasing or decreasing at least one of intensity and duration of an assistance torque in the walking assist profile such that the modifying increases the at least one of intensity and duration of the assistance torque in response to the current step of the user having the positive work properties in relation to the previous step and decreases the at least one of intensity and duration of the assistance torque in response to the current step of the user having the negative work properties in relation to the previous step; and
   controlling a driver to assist movements of the first joint and the second joint based on the modified walking assist profile.

11. The method of claim 10, wherein the modifying comprises:
   modifying the walking assist profile based on a value of at least one of a first joint angular velocity and a second joint angular velocity of the user when the first joint angle is same as the second joint angle, the first joint angular velocity and the second joint angular velocity being angular velocities associated with the first joint and the second joint, respectively.

12. The method of claim 11, wherein the modifying further comprises:
   modifying the walking assist profile such that the first joint angle and the second joint angle gradually change starting from a point in time when the first joint angle is the same as the second joint angle.

13. The method of claim 11, further comprising:
   determining that the current step of the user has the positive work properties in relation to the previous step if one of the first joint angular velocity and the second joint angular velocity is greater than the threshold while the first joint angle is same as the second joint angle.

14. The method of claim 11, further comprising:
   determining that the current step of the user has the negative work properties in relation to the previous step if one of the first joint angular velocity and the second joint angular velocity is less than the threshold while the first joint angle is same as the second joint angle.

15. The method of claim 10, wherein the walking assist profile indicates the assistance torque applied by the driver to at least one of the first joint and the second joint.

* * * * *